United States Patent [19]

Kerwar et al.

[11] Patent Number: 5,593,671
[45] Date of Patent: Jan. 14, 1997

[54] METHOD OF ATTENUATING LUNG CAPILLARY LEAK IN A MAMMAL

[75] Inventors: Suresh S. Kerwar, Ossining, N.Y.; Michael M. Wick, Brookline, Mass.

[73] Assignee: American Cyanamid Company, Wayne, N.J.

[21] Appl. No.: 269,702

[22] Filed: Jul. 1, 1994

[51] Int. Cl.$^6$ .......................... A61K 38/20; A61K 45/05; A61K 38/20; A61K 31/505
[52] U.S. Cl. .............................. 424/85.2; 514/12; 514/21; 514/258; 530/351; 544/260
[58] Field of Search ............................... 424/85.2; 514/2, 514/21, 740, 258; 530/357; 544/260

[56] References Cited

PUBLICATIONS

J. P. Seigel, R. K. Puri, Interleukin-2 Toxicity—Journal of Clinical Oncology, vol. 9, No. 4 (Apr.), 1991 pp. 694–704.
John T. Vetto et al, Reduction of Toxicity of Interleukin-2 and Lumpholine-Activated Killer Cells in Hmans by the Administration of Corticosteroids—Journal of Clinical Oncology, vol. 5 No. 3 (Mar.), 1987 pp. 496–503.
M. Z. Papa et al, Effect of Corticosteroid on the Antitumor Activity of Lympholine-activated Killer Cells and Interleukin-2 in Mice—Cancer Research 46, 5618–5623, Nov. 1986.
D. R. Seeger et al, Analogs of Peroylutamic Acid. III. 4–Amino Derivatives—May 1949 4–Amino Derivatives of pteroylglutamic Acid pp. 1753–1758.
M. V. Freeman, The Fluormetric measurement of the Absorption, Distribution and Excretiion of Single Doses of 4–Amino-10–Methyl Pteroylglutamic Acid (Amethopterin) in man—Clinical Pharmacology and Experimental Therapeutics Section, national Cancer Institute pp. 154–162.
E. S. Henderson et al, The Metabolic Fate of Tritiated methotrexate II. Absorption and Excretion in Man pp. 1018–1024.
P. T. Condit, Studies of the Folic Acid Vitamins. II. The Acute Toxicity of Amethopterin in Man and Studies on the Folic Acid Vitamins, III. The Duration of the Effects of Folic Acid Antagonists in Man—American Cancer Society 1960 vol. 13 pp. 221–235.
P. T. Condit, et al, Renal Toxicity of Methotrexate—Oklahmoma Medical Research Foundation, Jun. 3, 1968 pp. 126–131.
K. B. Bischoff, et al, Preliminary Model for Methotrexate Pharmacokinetics—Research Articles vol. 59 No. 2 Feb. 1970 pp. 149–154.
K. B. Bischoff, et al, Methotrexate Pharmacokinetics—Journal of Pharmaceutical Sciences—pp. 1128–1133.
W. E. Evans, Methotrexate—pp. 518–548.
J. R. Bertino, Clinical use of methotrexate–With Emphasis on use of High Doses—Cancer Treatment reports, vol. 65, Supplement 1, 1981 pp. 131–135.
J. Jolivet, et al, Medical progress, The Pharmacology and Clinical Use of Methotrexate—The New England Journal of Medicine, Nov. 3, 1983, pp. 1094–1104.

A. Weinstein, Methotrexate: A Perspective on Its Use for Rheumatoid Arthritis, Journal of Rheumatology Supplement No. 12, 1985—pp. 1–2.
J. R. Ward, Historical Perspective on the Use of Methotrexate for the Treatment of Rheumatoid Arthritis, Journal of Rheumatology Supplement No. 12, 1985 pp. 3–6.
D. E. Trentham, The Immunopathogenesis of Rheumatoid Arthritis, Journal of Rheumatology Supplement No. 12, 1985, pp. 7–10.
D. E. Furst, Clinical Pharmacology of Very Low Dose Methotrexate or Use in Rheumatoid Arthritis, Journal of Rheumatology Supplement No. 12, pp. 11–14.
W. E. Evans, M. K. Christensen, Drug Interactions with methotrexate—Journal of Rheumatology Supplement No. 12, 1985, pp. 15–20.
R. F. Willkens, Short Term Efficacy of Methotrexate in the Treatment of Rheumatoid Arthritis—Journal of Rheumatology Supplement No. 12, 1985, pp. 21–24.
J. M. Kremer, Longterm Methotrexate Therapy in Rheumatoid Arthritis: A Review—Journal of Rheumatology Supplement No. 12, 1985 pp. 25–28.
K. G. Tolman, et al, Methotrexate and the Liver—Journal of Rheumatology Supplement No. 12, pp. 29–34.
M. E. Weinblatt, Toxicity of Low Dose Methotrexate in Rheumatoid Arthritis—Journal of Rheumatology Supplement No. 12, 1985, pp. 35–39.
J. R. Ward, Summary, Journal of Rheumatology Supplement No. 12, 1985, pp. 40–44.
M. Rosenstein, Extravasation of Intravascular Fluid Mediated by the Systemic Administration of recombinant Interleukin 2—The Journal of Immunology, vol. 137, 1735–1742, Sep. 1, 1966.
Package Insert, Methotrexate Tablets, Methotrexate Sodium and Methotrexate LPF* Sodium Parenteral, May 1988.
D. L. Fraker, et al, Passive Immunizatin Against Tumor necrosis Factor partially Abrogates Interleukin 2 Toxicity—The Journal of Experimental Medicine vol. 170 Sep. 1989 pp. 1015–1020.
M. Fleisher, Antifolate Analogs: mechanism of Action, Analytical methodology, and Clinical Efficacy—Therapeutic Drug Monitoring, 15 pp. 521–526 1993.
K. S. Antman, et al, Effect of Recombinant Human Granulocyte–Macrophage Colony–Stimulating Factor on Chemotherapy–Induced Myelosuppression—The New England Journal of Medicine, vol. 319, No. 10, Sep. 1988, pp. 593–598.
S. J. Brandt, et al, Effect of Recombinant Human Granulocyte–Macrophage Colony–Stimulating Factor on Hematopoietic reconstitution After High–Dose Chemotherapy and Autologous Bone Marrow Transplantation, The New England of medicine, vol. 318, No. 14, Apr. 1988, pp. 869–876.
Package Insert, Proleukin Aldesleukin for Injection, Nov. 1992.

*Primary Examiner*—Ponnathapura Achutamurthy
*Attorney, Agent, or Firm*—T. G. Szatkowski; R. F. Boswell, Jr.

[57] ABSTRACT

The invention provides a method of attenuating lung capillary leak in a mammal by administering an effective amount of an antifolate, methotrexate.

9 Claims, No Drawings

METHOD OF ATTENUATING LUNG CAPILLARY LEAK IN A MAMMAL

FIELD OF THE INVENTION

This invention relates to a method of attenuating capillary leak in a mammal by administering an effective amount of an antifolate, methotrexate.

BACKGROUND OF THE INVENTION

Lung capillary leak syndrome is a dose limiting toxicity brought about by administration of cytokines, lymphokines, growth factors, recombinant proteins and the like to patients and it produces major morbidity. Lung capillary leak is due to an increase in vascular permeability and is manifested by multi-organ system dysfunction and generalized fluid accumulation and in particular the accumulation of fluid in the lung. Patients with lung capillary leak require respiratory and ventilatory support (see J. P. Siegel and R. K. Puri, Interleukin-2 toxicity, *Journal of Clinical Oncology*, Vol. 9, pp 694–704, 1991) adding to the expense of medical care. The most troublesome effect of lung capillary leak syndrome is the extravasation of fluid into the lungs, thereby producing interstitial pulmonary edema, often requiring the termination of cytokine, lymphokine, growth factor or protein therapy and the use of supplemental oxygen and other respiratory and ventilatory support measures.

Heretofore, corticosteroids have been utilized to attenuate lung capillary leak syndrome induced by the lymphokine Interleukin-2 (IL-2). However, the corticosteroids adversely affect the antitumor efficacy of the IL-2 (Vetto, J. T., M. Z. Papa, M. T. Loitze J. Clin. Oncol. 5:496–503 1987; Papa M. Z., J. T. Vetto, S. E. Ettinghausen, J. J. Mule and S. A. Rosenberg. Cancer Res. 46:5618–5623, 1986).

SUMMARY OF THE INVENTION

The present invention provides a method of attenuating lung capillary leak in a mammal which comprises administering to said mammal an amount of an antifolate, methotrexate, effective to attenuate lung capillary leak. The effective amount of the antifolate, methotrexate, is from about 0.025 mg/Kg to about 2.0 mg/Kg. The antifolate, methotrexate, is administered orally, intraperitoneally, subcutaneously or intraveneously.

The method of the present invention is particularly effective in attenuating lung capillary leak induced by the lymphokine, Interleukin-2. In utilizing the method of the present invention to attenuate lung capillary leak induced by Interleukin-2, the antifolate methotrexate is administered adjunct to the administration of the Interleukin-2. In particular the antifolate methotrexate is administered simultaneously with, prior to or after the intraperitoneal administration of IL-2.

The invention also provides a composition of matter containing an amount of methotrexate effective to attenuate lung capillary leak in a mammal in association with a pharmaceutically acceptable carrier.

DETAILED DESCRIPTION OF THE INVENTION

In accordance with the present invention, lung capillary leak in a mammal is attenuated by administering an effective amount of an antifolate methotrexate.

Methotrexate, is known as N-[4-[[(2,4-diamino-6-pteridinyl)methyl]methylamino]benzoyl]-L-glutamic acid and has the structural formula:

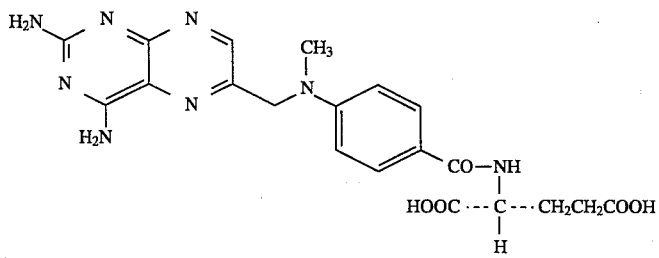

The following references describe the preparation of methotrexate (see Seeger et al., J.Am.Chem.Soc. 71, 1753(1949); the metabolism of methotrexate (see Freeman, J.Pharmacol.Exp.Ther. 122, 154(1958) and Henderson et al., Cancer Res. 25, 1008, 1018(1965)); the toxicity of methotrexate: Condit et al., Cancer 13, 222–249(1960), ibid. 23, 126(1969); the pharmacokinetic models of methotrexate: Bischoff, et al., J.Pharm.Sci 59, 149(1970); eidem, ibid. 60, 1128(1971); the metabolism and pharmacokinetics of methotrexate: W. E. Evans, Appl.Pharmacokinet. 1980, 518–548; the clinical pharmacology of methotrexate: J. R. Bertino, Cancer Chemother. 3, 359–375(1981); J. Jolivet et al., N.Engl.J.Med. 309, 1094–1104(1983) and the clinical experience of methotrexate in rheumatoid arthritis; J.Rheumatol. 12, Suppl, 12, 1–44(1985).

Methotrexate inhibits dihydrofolic acid reductase. Folic acid must be reduced to tetrahydrofolic acid by this enzyme in the process of DNA synthesis, repair and cellular replication. Therefore, methotrexate interferes with cellular reproduction. See methotrexate package insert, Lederle Laboratories, Pearl River, N.Y. 10965 and references therein. Methotrexate has not been reported heretofore to attenuate capillary leak.

The amount of the antifolate, methotrexate, effective to attenuate lung capillary leak in a mammal is from about 0.025 mg/Kg to about 2.0 mg/Kg. A preferred range is between 0.025 mg/kg to 0.5 mg/kg. The antifolate methotrexate is administered orally, intraperitoneally, subcutaneously or intraveneously. Oral administration is preferred.

A distinct advantage of the present invention is that attenuation of capillary leak by administering an effective dose of methotrexate will decrease the costs of hospital care. Patients need not be treated in intensive care units and respiratory and ventilatory support will not be required. Unlike corticosteroids, heretofore utilized to attenuate IL-2 induced lung capillary leak, methotrexate does not compromise the antitumor efficacy of IL-2. Thus, in addition, it may be possible to administer higher doses of IL-2 or other cytokine, lymphokine or protein such that the anticancer response rates may be increased.

Interleukin-2 (IL-2) is one of the first purified recombinant lymphokines to be administered to humans and is the most studied lymphokine for the treatment of certain human malignancies (renal cell carcinoma and melanoma). A dose limiting toxicity associated with IL-2 therapy for cancer is capillary leak in the lung.

The human recombinant interleukin-2 product PROLEUKIN® is a highly purified protein with a molecular weight of approximately 15,300 daltons. See package insert Chiron Corporation, Emeryville, Calif. and references therein. The chemical name is des-alanyl-1, serine-125 human interleukin-2. The product is produced by recombinant DNA technology using genetically engineered E. coli strain containing an analog of the human interleukin-2 gene. In vitro studies performed on human cell lines demonstrate the immunoregulatory properties of PROLEUKIN® including: a) enhancement of lymphocyte mitogenesis and stimulation of long-term growth of human Interleukin-2 dependent cell lines; b) enhancement of lymphocyte cytotoxicity; c) induction of killer cell lymphokine-activated (LAK) and natural (NK) activity; and d) induction of interferon-gamma production. When tested in vivo in select murine tumor models and in the clinic, PROLEUKIN® produces multiple immunological effects in a dose dependent manner. These effects include activation of cellular immunity with profound lymphocytosis, eosinophilia, and thrombocytopenia, and the production of cytokines including tumor necrosis factor, IL-1 and gamma interferon. In vivo experiments in murine tumor models have shown inhibition of tumor growth.

The efficacy of methotrexate in attenuating capillary leak induced by IL-2 is demonstrated by the murine model of IL-2 induced capillary leak (M. Rosenstein, S. E. Ettinghausen and S. A. Rosenberg, Extravasation of Intravascular Fluid Mediated by the Systemic Administration of Recombinant Interleukin-2, *Journal of Immunology*, Vol. 137, pp 1735–1742, 1986). Methotrexate is administered adjunct to the administration of IL-2. Such adjunct administration includes administration simultaneously, prior to and after administration of IL-2. For administration of methotrexate prior to IL-2 administration a time of from about 1 hour to about 5 hours prior to administration of IL-2 may be employed. A time of about 1 hour prior to IL-2 administration is preferred.

Male C57/B16 mice (Charles River, Wilmington, Mass.) are used. Human IL-2, PROLEUKIN® (specific activity $16.4 \times 10^6$ IU/mg) is purchased from Cetus Oncology Products, Emeryville, Calif. Mice are treated intraperitoneally with 9 doses of IL-2 (500,000 IU/dose) over a four day period. Two doses of IL-2 are administered on day 1, three doses on day 2 and day 3 and a single dose on day 4. Three hours after the last dose of IL-2, mice are injected intravenously with 1.0 µCi of $^{125}$Iodinated bovine serum albumin. One hour after radioactive albumin administration, the mice are weighed, sacrificed and an aliquot of blood is collected for analysis of radioactivity. The lungs are flushed with two ml of phosphate buffered saline (PBS), excised, blotted, weighed and analyzed for radioactivity. Radioactivity measurements are conducted with a gamma counter and the results are shown as counts per minute (cpm).

To ascertain the effect of methotrexate on IL-2 induced capillary leak, doses of 0.5 mg/Kg or 0.25 mg/Kg or 0.125 mg/Kg of methotrexate are administered orally one hour before each dose of IL-2 (hence 9 doses of methotrexate are administered over the four day period each one being administered one hour before each administration of IL-2). Methotrexate is obtained from Clinical Research Section, Lederle Laboratories, Pearl River, N.Y. Results of this experiment are described in Table 1.

TABLE 1

| Group | Body Wts (gm ± SE) | Lung Wts (mg ± SE) | cpm in lung (±SE) | cpm in blood (±SE) |
|---|---|---|---|---|
| Phosphate Buffered Saline (PBS) Control | 19 ± 0.2 | 137 ± 3 | 13,450 ± 1026 | 7122 ± 202 |
| IL-2 alone** | 19 ± 0.2 | 175 ± 10* | 24,205 ± 2744* | 6899 ± 357 |
| methotrexate (0.5 mg/kg) followed in 1 hour by IL-2** | 19 ± 0.2 | 138 ± 5† | 15,806 ± 1141† | 7069 ± 254 |
| methotrexate (0.25 mg/kg) followed in 1 hour by IL-2** | 19 ± 0.3 | 140 ± 3† | 16,194 ± 1218† | 7240 ± 252 |
| methotrexate (0.125 mg/kg) followed in 1 hour by IL-2** | 19 ± 0.2 | 146 ± 5† | 18,099 ± 2248 | 6527 ± 596 |

*Significantly different from control mice that received phosphate buffered saline (PBS). (Student t test, p <0.05).
†Significantly different from the IL-2 group (student t test, p <0.05).
**Each dose of IL-2 = 500,000 IU.
Each group contains 10–15 mice. SE = standard error of the mean.

Because increase in lung weights and radioactivity accumulating in the lung are parameters used to demonstrate IL-2 induced capillary leak in mice (M. Rosenstein, S. E. Ettinghausen and S. A. Rosenberg, Extravasation of Intravascular Fluid Mediated by the Systemic Administration of Recombinant Interleukin-2, *Journal of Immunology*, Vol. 137, pp 1735–1742, 1986), the results shown above indicate that methotrexate is exceptionally effective in attenuating capillary leak induced by IL-2. Lung weights and radioactivity accumulating in the lung are significantly lower for mice pretreated with methotrexate when compared to the mice in the IL-2 group. As shown in the above Table 1 the minimal effective dose of methotrexate is 0.25 mg/kg administered orally, one hour before IL-2 treatment. Radioactivity present in the blood is similar in all groups indicating that an equivalent amount of radioactive albumin is administered to mice in the various treatment groups.

Using the same testing protocol as described above, a single daily dose of 0.5 mg/Kg or 1 mg/Kg or 2 mg/Kg of methotrexate administered one hour before the administration of the first daily dose of IL-2 is also effective in the attenuation of capillary leak induced by IL-2.

Male C57/B16 mice (Charles River, Wilmington, Mass.) are used. Human IL-2, PROLEUKIN® (specific activity $16.4 \times 10^6$ IU/mg) is purchased from Chiron Corporation, Emeryville, Calif. Mice are treated intraperitoneally with 9 doses of IL-2 (500,000 IU/dose) over a four day period. Two doses of IL-2 are administered on day 1, three doses on day 2 and day 3 and a single dose on day 4. A single daily dose of methotrexate was administered orally one hour before the first IL-2 dose. Therefore four doses of methotrexate were administered over the four day period. Three hours after the last dose of IL-2, mice are injected intravenously with 1.0 μCi of $^{125}$Iodinated bovine serum albumin. One hour after radioactive albumin administration, the mice are weighed, sacrificed and an aliquot of blood is collected for analysis of radioactivity. The lungs are flushed with two ml of phosphate buffered saline (PBS), excised, blotted, weighed and analyzed for radioactivity. Radioactivity measurements are conducted with a gamma counter and the results are shown as counts per minute (cpm). Results of this experiment are shown in Table 2.

methotrexate on IL-2 induced capillary leak is not schedule dependent. Therefore single or multiple dosing regimens known to those skilled in the art can be utilized to deliver a therapeutically effective dose of methotrexate. In addition, the timing of methotrexate administration relative to IL-2 treatment can be adjusted so as to achieve the maximal beneficial effect of reduction in capillary leak. A preferred regimen is to orally administer 0.025 mg/Kg to 2.0 mg/Kg of methotrexate 1 to 5 hours before the administration of IL-2. Most preferred is to orally administer 0.025 mg/Kg to 0.5 mg/Kg of methotrexate 1 hour before the administration of IL-2. The most particularly preferred regimen is to orally administer 0.5 mg/Kg of methotrexate 1 hour before administration of IL-2.

Corticosteroids have heretofore been used in this murine model to treat capillary leak, however, treatment with this agent compromises the antitumor effect of IL-2 (M. Z. Pappa, J. T. Vetto, S. E. Ettinghausen, J. J. Mule and S. A. Rosenberg. Effect of Corticosteroids on the Antitumor Activity of Lymphokine Activated Killer Cells and Interleukin-2 in Mice. *Cancer Research*, Vol. 46, pp 5618–5623, 1986).

In contrast to corticosteroids, methotrexate does not interfere with the efficacy of IL-2 as shown by the results using the following protocol:

Male C57/B16 mice are injected intravenously with $1 \times 10^4$ cells derived from MCA-205 tumors. Earlier studies have demonstrated that these tumor cells derived from methyl cholanthrene induced carcinoma (ex., MCA-105 or MCA-205) respond to IL-2 therapy (M. Z. Pappa, J. T. Vetto,

TABLE 2

|  | body weights (gm ± SE) | lung wt (mg ± SE) | cpm in lungs (±SE) | cpm in blood (±SE) |
|---|---|---|---|---|
| Phosphate Buffered Saline (PBS) control | 18.5 ± 0.2 | 127 ± 2 | 11,904 ± 1239 | 8046 ± 356 |
| IL-2** | 19.2 ± 0.3 | 167 ± 4* | 19,371 ± 1755* | 6902 ± 348 |
| single dose of methotrexate (2 mg/kg) prior to daily IL-2 therapy** | 18.6 ± 0.3 | 136 ± 8† | 13,103 ± 962† | 7698 ± 196 |
| single dose of methotrexate (1 mg/kg) prior to daily IL- therapy** | 17.8 ± 0.3 | 129 ± 3† | 13,623 ± 1333† | 7850 ± 509 |
| single dose of methotrexate (0.5 mg/kg) prior to daily IL- therapy** | 18.3 ± 0.2 | 142 ± 6† | 12,219 ± 1111† | 8160 ± 170 |

*p <0.05 as compared to phosphate buffered saline (PBS) control, student t test.
†p <0.05 as compared with IL-2 group.
SE = standard error of the mean.
n = 10 per group
**Each dose of IL-2 = 500,000 IU.

Since methotrexate administration regimens may fall into two categories (single or multiple doses), the two experiments described above indicate that the beneficial effect of S. E. Ettinghausen, J. J. Mule and S. A. Rosenberg. Effect of Corticosteroids on the Antitumor Activity of Lymphokine Activated Killer Cells and Interleukin-2 in Mice. *Cancer*

*Research*, Vol. 46, pp 5618–5623, 1986). After 24 hr, MCA-205 treated mice are divided into groups (n=5/group). One group of mice is treated with phosphate buffered saline (PBS control). A second group of mice is treated with 500,000 IU of IL-2 three times daily. Still other groups of mice are treated with oral doses of 0.5 mg/Kg or 0.25 mg/Kg of methotrexate three times daily followed in 1 hour by IL-2. A total of 15 doses of IL-2 or IL-2 plus methotrexate are administered over a five day period. Methotrexate is administered orally one hour before each dose of IL-2. After 5 days of therapy, mice are sacrificed, the lungs stained with India ink (to reveal tumors) and destained with Fekettes solution. The lungs are then scored for the number of tumor nodules present. This protocol for determining the efficacy of IL-2 is adapted from a protocol used by Fraker et al (D. L. Fraker, J. Langstein, J. A. Norton, Passive Immunization Against Tumor Necrosis Factor Partially Abrogates Interleukin-2 Toxicity, *Journal of Experimental Medicine*, Vol. 170, pp 1015–1020, 1989). The results of this experiment are shown in Table 3:

TABLE 3

| GROUP | NUMBER OF MICE | NUMBER OF TUMOR NODULES/LUNG (±SE) |
|---|---|---|
| Control (PBS) | 5 | 68 ± 19 |
| IL-2** | 5 | 9 ± 4* |
| Methotrexate (0.5 mg/kg) followed in 1 hour by IL-2** | 5 | 6 ± 1* |
| Methorexate (0.25 mg/kg) followed in 1 hour by IL-2** | 5 | 15 ± 6* |
| Methotrexate alone (0.5 mg/kg) | 5 | 34 ± 14† |
| Methotrexate alone (0.25 mg/kg) | 5 | 27 ± 9† |

*Significantly different from control group, p <0.05, student t test;
SE = standard error.
†Not different from control group, student t test.
**Each dose of IL-2 = 500,000 IU The above experiment indicates that methotrexate does not interfere with the efficacy of IL-2 in this IL-2 responsive murine tumor model. Therefore, it is expected that in patients receiving IL-2 therapy, the efficacy of IL-2 will not be compromised and the capillary leak induced by IL-2 will be attenuated. In addition, the above results indicate that methotrexate in the absence of IL-2 does not exhibit anti-tumor properties in this animal model.

The mechanism of action of methotrexate in attenuating lung capillary leak in the above experiments has not been established. However, methotrexate is known to inhibit the enzymatic activity of dihydrofolate reductase (M. Fleisher, Antifolate Analogs, Mechanism of Action, Methodology and Clinical Efficacy. *Therapeutic Drug Monitoring*, Vol. 15, pp 521–526, 1993). When methotrexate is administered to a mammal, it is also converted to methotrexate polyglutamate and polyglutamates of methotrexate are also known to inhibit other enzymes for example 5-aminoimidazole-4-carboxamide ribonucleotide transformylase that require tetrahydrofolate as a cofactor. It is therefore contemplated that other inhibitors of dihydrofolate reductase, such as (ex. Trimetrexate®, Edatrexate®) or inhibitors of 5-aminoimidazole-4-carboxamide ribonucleotide transformylase will also be useful in attenuating lung capillary leak.

It is contemplated that capillary leak induced by other cytokines, lymphokines, growth factors and other recombinant proteins (K. S. Antman, J. D. Griffin, A. Elias et al Effect of Recombinant Human Granulocyte Macrophase Colony Stimulating Factor on Chemotherapy Induced Myelosuppression. *New England J. Med.*, Vol. 319: 593–598, 1988; S. J. Brandt, W. P. Peters, S. K. Atwater et al, Effect of Human Granulocyte Macrophage Colony Stimulating Factor on Hematopoietic Reconstitution After High Dose Chemotherapy and Autologous Bone Marrow Transplantation, *New Eng. J. Med.*, Vol. 318: 869–876, 1988) may also be attenuated by the administration of an antifolate methotrexate.

Methotrexate may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, methotrexate may be incorporated with excipients and used in the form of ingestible tablets, buccal tablets, troches, capsules, elixers, suspension, syrups, wafer, and the like. Such compositions and preparations should contain at least 0.05% of methotrexate. The percentage of the compositions and preparations may, of course, be varied and may conveniently be between about 2 to 60% of the weight of the unit. The amount of methotrexate in such therapeutically useful compositions is such that a suitable dosage will be obtained. Preferred compositions or preparations according to the present invention are prepared so that an oral dosage unit form contains between 0.025 and 2.0 mg of methotrexate.

The tablets, troches, pills, capsules and the like may also contain the following: a binder, such as gum tragacanth, acacia, corn starch or gelatin; excipients such as dicalciumphosphate; a disintegrating agent such as corn starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to material of the above type, a liquid carrier. Various other material may be present as coating or to otherwise modify the physical form of the dosage unit. For instance, tablets, pills, or capsules may be coated with shellac, sugar or both. A syrup or elixer may contain methotrexate, sucrose as a sweetening agent, methyl and propylparabens as preservative, a dye and flavoring such as cherry or an orange flavor. Of course, any material used in preparing any dosage unit form should be pharmaceutically pure and substantially non-toxic in the amounts employed. In addition, methotrexate may be incorporated into sustained-release preparations and formulations.

Methotrexate may also be administered parenterally or intraperitoneally. Solutions of methotrexate can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. The form must be stable under the conditions of manufacture and storage and must be preserved against the contamination action of microorganisms such as bacteria and fungi. The carrier can be a solvent or dispersion medium containing, for example, water, ethyl alcohol, polyol (for example, glycerol, propylene glycol, and liquid polyethylene glycol and the like), suitable mixtures thereof, and vegetable oils. The proper fluidity can be maintained, for example, by the use of a coating such as lecithin, by the maintenance of the required particle size in the case of dispersion and the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating methotrexate in the required amount in the appropriate solvent with various of the other ingredients enumerated above, as required, followed by filtered sterilization. Generally, dispersions are prepared by incorporating methotrexate into a sterile vehicle which contains the basic dispersion medium and the required other ingredients from those enumerated above. In the case of sterile powder, for the preparation of sterile injectable solutions, the preferred methods of preparation are vacuum drying and the freeze-drying technique which yield a powder of methotrexate, plus any additional desired ingredient from a previously sterile-filtered solution thereof.

As used herein, "pharmaceutically acceptable carrier" includes any and all solvents, dispersion media, coating, antibacterial and antifungal agents, isotonic and absorption delaying agents and the like. The use of such media and agents for pharmaceutically active substances is well known in the art. Except insofar as any conventional media or agent is incompatible with the active ingredient, it's use in the therapeutic compositions is contemplated. Supplementary active ingredients can also be incorporated into the compositions.

It is especially advantageous to formulate parenteral compositions in dosage unit form for ease of administration and uniformity of dosage. Dosage unit from as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of methotrexate and the particular therapeutic effect to be achieved (attenuation of lung capillary leak syndrome) and (b) the limitations inherent in the art of compounding methotrexate for the lung capillary leak syndrome in living subjects having a diseased condition in which bodily health is impaired as herein disclosed in detail.

Methotrexate is compounded for convenient and effective administration in effective amounts with a suitable pharmaceutically acceptable carrier in dosage unit form as herein before disclosed. A unit dosage form can, for example, contain methotrexate in amounts ranging from about 0.1 to 400 mg, with from 1 to 20 mg being preferred. Expressed in proportions, methotrexate is generally present in from about 0.1 to about 40 mg/ml of carrier. In the case of compositions containing supplementary active ingredients, the dosages are determined by reference to the usual dose and manner of administration of the said ingredients.

A single intravenous dosage, slow constant infusion, or repeated daily dosages can be administered. Daily dosages up to about 1 to 10 days are often sufficient. It is also possible to dispense one daily dosage or multiple daily doses or one dose on alternate or less frequent days. As can be seen from the dosage regimens, the amount of methotrexate administered is to be sufficient to attenuate Interleukin-2 induced pulmonary capillary leak syndrome.

We claim:

1. A method of attenuating lung capillary leak in a mammal induced by the administration of interleukin-2 which comprises administering to said mammal an amount of methotrexate effective to attenuate lung capillary leak.

2. The method of claim 1 wherein said effective amount of methotrexate is from about 0.025 mg/kg to about 2.0 mg/kg.

3. The method of claim 1 wherein said methotrexate is administered orally, intraperitoneally, subcutaneously or intravenously.

4. The method of claim 1 wherein said methotrexate is administered orally.

5. The method of claim 1 wherein the administration of methotrexate is in conjunction with the administration of Interleukin-2.

6. The method of claim 1 wherein said methotrexate is administered simultaneously with said administration of Interleukin-2.

7. The method of claim 1 wherein said methotrexate is administered prior to said administration of Interleukin-2.

8. The method of claim 7 wherein said methotrexate is administered from about 1 to about 5 hours prior to administration of Interleukin-2.

9. The method of claim 8 wherein said methotrexate is administered about 1 hour prior to administration of Interleukin-2.

* * * * *